US006334999B1

(12) United States Patent
Gilbert et al.

(10) Patent No.: US 6,334,999 B1
(45) Date of Patent: Jan. 1, 2002

(54) LIPOSOMAL AEROSOLS FOR DELIVERY OF CHEMOTHERAPEUTIC RETINOIDS TO THE LUNGS

(75) Inventors: Brian E. Gilbert; Ranjani Parthasarathy; Kapil Mehta, all of Houston, TX (US)

(73) Assignee: Research Development Foundation, Carson City, NV (US)

( * ) Notice: Subject to any disclaimer, the term of this patent is extended or adjusted under 35 U.S.C. 154(b) by 0 days.

(21) Appl. No.: 09/385,104

(22) Filed: Aug. 27, 1999

(51) Int. Cl.[7] .................................................. A61K 9/12
(52) U.S. Cl. .......................... 424/45; 424/450; 424/46; 514/725
(58) Field of Search ........................... 424/45, 46, 450; 514/725

(56) References Cited

U.S. PATENT DOCUMENTS 5,958,378 A * 9/1999 Waldrep et al.
6,090,407 A * 7/2000 Knight et al.

OTHER PUBLICATIONS

Hans Schreier et al. (1993). *Journal of Controlled Release*, 24: 209–223.*

* cited by examiner

Primary Examiner—Raj Bawa
(74) Attorney, Agent, or Firm—Benjamin Aaron Adler (57) ABSTRACT

To optimize the delivery of all-trans retinoic acid to lung tissue, the potential of vehiculating this drug in liposomes and delivering it via aerosol was determined. Liposomes provide a means to prevent local irritation of lung tissue, reduce pulmonary toxicity, prolong therapeutic levels, and generate high drug concentrations at the tumor sites. Therefore, the delivery of ATRA to the lung tissue in mice was accomplished by nebulization of L-ATRA. The liposomes in the aerosol were uniform, stable, and retained the drug well. The drug was effectively delivered at high concentrations to the lungs of mice and was retained at least up to 96 h after a single exposure to L-ATRA aerosols. The aerosol-delivered ATRA was biologically active as demonstrated by its ability to induce the expression of tissue-type transglutaminase. Aerosol delivery of L-ATRA offers an effective way to deliver high levels of ATRA to the lung without apparent pulmonary toxic effects.

15 Claims, 6 Drawing Sheets

(1 of 6 Drawing Sheet(s) Filed in Color)

LIPOSOMAL AEROSOLS FOR DELIVERY OF CHEMOTHERAPEUTIC RETINOIDS TO THE LUNGS

FEDERAL FUNDING LEGEND

This invention was produced in part using funds from the Federal government under grant no. FDR000923. Accordingly, the U.S. government has certain rights in this invention.

BACKGROUND OF THE INVENTION

1. Field of the Invention

The present invention relates generally to the fields of cancer biology, pharmacology, and chemotherapy. More specifically, the present invention relates to delivery of chemotherapeutic retinoids to the lungs by aerosolized liposomes.

2. Description of the Related Art

Retinoids are natural and synthetic analogs of vitamin A that normally play critical roles in growth, vision, reproduction, differentiation, and immune functions (1, 2). A relationship between vitamin A and cancer was first noted when experimentally induced vitamin A deficiency was shown to lead to preneoplastic lesions and neoplasms (3, 4). Retinoids modulate the in vitro growth and differentiation of a variety of transformed cell types, including melanomas, leukemias, and squamous carcinomas (1, 2, 5–7, 9, 10). Based on this property, retinoids have been used effectively in therapeutic regimens for prevention and treatment of various dermatological conditions, acute promyelocytic leukemia, as well as squamous cell carcinomas (SCC) of the aerodigestive tract, skin and cervix (6, 7, 10).

Epithelial tissues undergo biochemical, morphological and functional changes if deprived of or treated with an excess of retinoids. Because squamous cell carcinomas are derived from epithelial cells, they may be ideal targets for treatment with retinoids. Epithelial cancers of the head and neck or lungs are a devastating group of diseases that account for approximately 30% of cancer deaths (8). Retinoids are known to be potent modulators of epithelial differentiation and carcinogenesis (9). For example, 13-cis-retinoic acid is potent in suppressing oral carcinogenesis as well as preventing second primary tumors (10). Clinical trials using retinoic acid for the treatment of oral leukoplakia, a premalignant lesion of oral cancer, showed regression of existing disease and prevention of new disease and progression of the disease (11). This effect i s reversed when the treatment is withdrawn.

However, like many anticancer drugs, administration of ATRA is associated with undesirable toxic effects both in experimental models and in patients (11, 12). Liposomes have been evaluated both clinically and experimentally as a delivery system for mitigating the toxic effects associated with administration of drugs such as doxorubicin, vincristine, amphotericin, and retinoids (13–17). Liposomal incorporation of retinoids may provide an alternative way of delivering retinoids without the resulting toxic effects. The potential advantages of liposome delivery include increased activity due to specific targeting, sequestration of the drug at the target site, protection of the drug from rapid metabolism, amplified therapeutic effect due to packaging of numerous drug molecules in each liposome, and decreased toxicity due to altered pharmacokinetics (18–21). For example, free ATRA when administered in CD-1 mice, exerted toxic effects at 25–30 mg/kg of body weight. However, in liposome-encapsulated form the animals could tolerate much higher doses of ATRA (120 mg/kg) probably due to altered drug distribution in target tissues (16).

In a test of fourteen different formulations of liposomes, those composed of dipalmitoylphosphatidylcholine (DPPC) and stearylamine (SA) seemed to be the least toxic (13). The addition of the positive-charged SA dramatically increased uptake of L-ATRA, which was also well retained over a 24 hour period by squamous carcinoma cells. The L-ATRA was also biologically active and caused the differentiation of the cells in culture as well as in a spheroid model (13). Liposomal incorporation was also seen to reduce the rate of cellular and microsomal metabolism of ATRA. The amount of metabolites secreted into the medium was decreased by 15%, and the levels of intact ATRA in the cells doubled. Thus, liposomes were able to protect the drug from the metabolic enzymes of the cells (20). Microsomes isolated from the livers of free ATRA-treated rats catabolize [$^3$H] ATRA faster than microsomes isolated from L-ATRA-treated rats (18). Similarly, in leukemia patients, the plasma drug levels are maintained over long periods of time following administration of L-ATRA (19).

Retinoic acid is currently being administered to patients as an oral formulation. This would probably allow only very low levels of the drug to reach the tumor sites in the aerodigestive tract and lungs. Oral administration of retinoids allows only low levels of drugs to reach the aerodigestive tract especially the lungs. L-ATRA can be administered intravenously, but due to its particulate nature, a major fraction of the dose is taken up by the reticuloendothelial system. If the drug could be targeted directly to the aerodigestive tract, much higher concentrations of the drug could be achieved with minimal toxicity. The advantage of the aerosol mode of delivery is that the drug is deposited more uniformly over the respiratory tract, leading to local levels of the drug that may far exceed the levels achieved by systemic administration (22). However, free ATRA due to its lipophilic properties cannot be aerosolized.

The prior art is deficient in the lack of a means to deliver ATRA directly to the lungs. The present invention fulfills this longstanding need and desire in the art.

SUMMARY OF THE INVENTION

In one embodiment of the current invention, a method is described for the delivery of chemotherapeutic retinoids to the aerodigestive tract. The retinoid is incorporated into liposomes which are resuspended as an aqueous suspension. The resulting suspension is then aerosolized and inhaled by the animal or individual in need of such treatment.

In a preferred embodiment, the retinoid is all-trans-retinoic acid (ATRA), 13-cis retinoic acid, 9-cis retinoic acid, or 4-HPR. The retinoid is incorporated into the liposomes at a concentration of 0.1 to 10 mg/ml. After formation of the aerosol, the dose of the retinoid ranges from 1 to 100 µg retinoid per liter of aerosol. It is expected that this treatment shall result in a lung accumulation of 0.05 to 20 µg retinoid/gram of lung tissue.

In one embodiment of the present invention, the liposomes are composed of dipalmitoylphosphatidylcholine (DPPC) and stearylamine (SA). A dipalmitoylphosphatidylcholine to stearylamine ratio of 9:1 w/w is an appropriate formulation.

Likewise, in the preferred embodiment, the retinoid is incorporated into said liposomes at a drug:lipid ratio of 1:10 (w/w).

One method of forming the aerosol is with a jet type nebulizer. An appropriate aerosol can be formed by operating said nebulizer at a flow rate of 10 liters/minute for 30 minutes Aerosolization is carried out to obtain aerosol particles with mass median aerodynamic diameters of 1 to 3 microns. The liposomes within the aerosol have diameters falling within the 100 to 1000 n m range. The aerosol can then be inhaled for a period of time ranging from 5 minutes to 2 hours.

The treatment can be applied to any tumors of the aerodigestive tract but is especially useful for the treatment of tumors of the lungs. A series of treatments will be administered to maintain at a retinoid level in the lungs of 0.05 to 20 µg retinoid/gram of lung tissue. The frequency of the treatments may be multiple times per week. It is also possible to administer a systemic dose of retinoid by absorption through the lungs.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIGS. 2A and 2B show ATRA levels (µg/g) in the lungs of mice exposed to a single dose of aerosolized L-ATRA. Mice exposed to aerosols were sacrificed (four mice/time point) at the indicated time points, the lungs were removed, and the drug was extracted and analyzed by HPLC. FIG. 2A demonstrates the accumulation of ATRA after a short period of time (8 hours) following a single exposure to aerosolized L-ATRA. FIG. 2B shows the accumulation after an extended period of time (96 hours). Values shown are the means of ATRA levels (µg/g of lung tissue) from at least three animals.

FIGS. 4A and 4B demonstrate the results of treating mice with the aerosolized L-ATRA.

FIGS. 5A and 5B show uptake of fluorescent lipid-tagged L-ATRA by alveolar macrophages lavaged from mice exposed to a single treatment of aerosols containing L-ATRA. (FIG. 5A) phase-contrast microscopy, (FIG. 5B) fluorescent microscopy.

DETAILED DESCRIPTION OF THE INVENTION

The current invention is directed to the delivery of chemotherapeutic retinoids to the aerodigestive tract, especially the lungs. This is accomplished by forming liposomes containing an appropriate concentration of a retinoid. After resuspension of the liposomes in an aqueous suspension, the liposomes are delivered to the aerodigestive tract as an aerosol which is inhaled by the animal or individual in need of such treatment.

The current invention is especially directed to the administration of all-trans-retinoic acid (ATRA), 13-cis retinoic acid, 9-cis retinoic acid, or 4-HPR. An appropriate concentration of etinoid in the liposomes is 0.1 to 10 mg/ml. The liposomes can be suspended and nebulized so that the aerosol is delivered as 1–100 µg retinoid per liter of aerosol. It is desired that this administration should result in an retinoid accumulation in the lungs of 0.1 to 20 µg retinoid/gram of lung tissue.

While many different liposomal compositions are possible, liposomes composed of dipalmitoylphosphatidylcholine (DPPC) and stearylamine (SA) at a ratio of 9:1 w/w were found to be especially effective. All-trans-retinoic acid was incorporated into such liposomes at a drug:lipid ratio of 1:10 (w/w) which resulted in a final 0.5 mg/ml concentration of retinoid in the liposomes.

The aerosol can formed with a jet type nebulizer at a flow rate of 10 liters/min for 30 minutes to result in aerosol particles with aerodynamic diameters of 1 to 3 microns. Liposomes sizes ranging from 100 to 1000 nm were observed in the resulting aerosol. This aerosol is inhaled for a period of time ranging from five minutes to two hours.

The instant invention can be applied to the treatment of various tumors of the aerodigestive tract. It is especially expected to be valuable in the treatment of tumors of the lungs. A series of weekly treatments can be administered to maintain an retinoid dose of at least 0.05 to 20 µg retinoid/gram of lung tissue. It is also possible to use absorption through the lungs to administer a systemic dose of the retinoid.

The following examples are given for the purpose of illustrating various embodiments of the invention and are not meant to limit the present invention in any fashion.

EXAMPLE 1

Mice

Age-matched ICR male mice (8 weeks old, weighing 23 25 g) were purchased from Harlan-Sprague (Houston, Tex.) and housed in cages. They were fed mouse chow and water ad libitum.

EXAMPLE 2

Preparation of Liposomes

Multilamellar liposomes were prepared from lyophilized powder of the lipids dipalmitoylphosphatidylcholine (DPPC) and tearylamine (SA) (Avanti Polar Lipids, Alabaster, Ala.) in the ratio of 9:1 w/w. The lipids and ATRA (Argus Pharmaceuticals Inc., Woodlands, Tex.) in a drug:lipid ratio of 1:10 (w/w) were dissolved in tertiary butanol. The drug-lipid mixture was then freeze-dried in a lyophilizer and stored away from light at −20° C. (13).

Before use, the liposomes were reconstituted in 10 ml water, vortexed, and incubated at a temperature higher than the transition temperature of the lipids (>42° C.) for about 15–20 min in a water bath and were sonicated for about 20 min. The final drug concentration was 0.5 mg of ATRA/ml. The size of liposomes before and after aerosolization was determined by a Nicomp Submicron Particle Sizer-Model 370 (Nicomp, Santa Barbara, Calif.). To some vials, ≅0.5% (w/w) of fluorescent lipid (Rhodamine-PC; Avanti Lipids) was added before lyophilization.

EXAMPLE 3

Aerosol Delivery

A jet type nebulizer (Puritan-Bennett Co., Los Angeles, Calif.) was used to generate aerosol particles of the L-ATRA. The nebulizer has a single air jet and a 10 ml reservoir and generated an air flow of 10 liter/min. Each preparation was placed in the reservoir and aerosolized for 25–30 min. Groups of 10–25 mice were placed in special air-tight cages and allowed to inhale the aerosols for 30 min. At different time points ranging from 15 minutes to 96 hours, four animals at each time point were removed from the cage and killed by cervical dislocation. Untreated mice were used as controls. For multiple-dose treatment, animals were exposed for 30 min to aerosolized L-ATRA every day for 5 consecutive days. After each treatment, the mice were sacrificed to collect the lungs for later analysis.

EXAMPLE 4

Quantitation of ATRA and Lipids by HPLC

ATRA was quantified by reverse-phase high-performance liquid chromatography (HPLC) with monitoring at 350 nm (Millipore Corp., Millford, Mass.). All measurements were made at ambient temperature on a stainless-steel HPLC column ($\mu$Bondapak C18 3.9×300 mm column; Millipore Corp.). The mobile-phases were 100% methanol (solvent B) and methanol:water (65:35) containing 10 mM ammonium acetate and 0.05% formic acid (solvent A). The solvents were set-up on a linear gradient at a flow rate of 2 ml/min. ATRA had a retention time of 25–26 min at 70% of solvent B and 30% of solvent A. This assay system was able to detect ATRA at 1.0 $\mu$g/ml and was linear up to 200 $\mu$g/ml concentration.

Lipids were also quantitated by an HPLC protocol followed by Vidgren et al (23). A Waters 717 WISP automatic sampler injector and a Spherisorb S5 amino column (25 cm×4.66 mm, 5 $\mu$m) were used with acetonitrile, methanol, and 10 mM ammonium/trifluoroacetic acid, pH 4.8 (64:28:8 v/v) as the mobile phase. Peaks were detected with a mass evaporative detector (Sedex 55, Sedere, France) and qualified with an integrator. 50 $\mu$l of each aerosol sample in methanol was injected and the DPPC in each sample was analyzed.

EXAMPLE 5

Characterization of Aerosol Particles of L-ATRA

Aerosol particle size was determined using an Andersen Cascade Impactor (Andersen Samplers Inc., Atlanta, Ga.). Calculations of aerodynamic mass median diameter and geometric standard deviation were based on gravimetric and chemical determinations of samples collected over a 5-min sampling period (24). The ATRA and the lipids deposited on the filters were obtained by soaking and shaking the filters in 10 ml of absolute methanol for about 1 hour. Total concentrations of ATRA and the lipids in the aerosol were determined by collecting 2 min aerosol samples in all-glass impingers containing 20 ml of water. The all-glass impingers were calibrated to collect 12.5 liter of air/minute. The concentrations of ATRA and lipids in the samples collected were determined by HPLC as described above.

EXAMPLE 6

Collection of Samples from Mice

At pre-determined time points, aerosol-treated and untreated animals were killed by cervical dislocation. Blood was drawn by cardiac puncture and the lungs and livers were removed. The tissues were homogenized in buffer (10 mM EDTA, 200 mg ascorbic acid, and 2 ml acetic acid in 200 ml of distilled water) and retinoic acid was extracted twice in methanol containing antioxidant (1 mg of butahydroxytouluene/ml). The buffer and methanol extracts were then dried together and reconstituted in 300 $\mu$l of methanol, of which 25 $\mu$l sample was used for HPLC analysis.

EXAMPLE 7

Biological Activity of L-ATRA

To study the biological activity of the aerosol-delivered L-ATRA, alveolar macrophages were obtained from the lungs of control and treated mice. Briefly, the lung tissue was placed on ice and lavaged 2–3 times with cold RPMI medium. The cells obtained from five animals with similar treatment were pooled and centrifuged. The cell pellet was then resuspended in RPMI medium containing 10% fetal calf serum and incubated for about 2 h in a 6-well plate. After incubation, nonadherent cells were removed by washing the wells twice with medium and the adherant cells were scraped into PBS. The cells were then centrifuged and the pellet resuspended in lysing buffer (phosphate-buffered saline, (PBS) containing 0.5% Triton X-100), sonicated, and assayed for transglutaminase (TGase) activity as described earlier (25). The cell lysates were also analyzed for TGase levels by immunoblotting, using a monospecific monoclonal antibody (CUB74, Neomarkers, Fremont, Calif.) as previously described (25). Alternatively, alveolar macrophages were allowed to adhere to plastic coverslips for 2 h. After the coverslips were washed, the macrophages were observed under fluorescent microscope for the uptake of fluorescent-lipid tagged liposomes.

EXAMPLE 8

Toxicity Studies

Tissue sections were fixed in buffered formalin, embedded in paraffin, and cut into 10-$\mu$M thick sections. Lung sections obtained from untreated and treated mice were observed for histological changes after staining with haematoxylin and eosin. Serum was isolated from treated and untreated animals and assayed for liver enzymes (SGOT, SGPT). Frozen sections of mice lungs were also taken before and after aerosolized L-ATRA treatments for visualization of fluorescent-lipid tagged liposomes in the lungs.

EXAMPLE 9

Characteristics of Aerosol L-ATRA

Liposomes used for aerosolization were made of the neutral lipid dipalmitoylphosphatidylcholine and the positively charged lipid stearylamine in the ratio of 9:1 (w/w). The drug to lipid ratio was 1:10, with a final concentration of ATRA at 0.5 mg/ml. On reconstitution, liposomes measured 807±165 nm on average, and after 20–30 min of aerosolization with the Puritan-Bennett Raindrop jet type nebulizer, they measured 309±138 nm in the aerosol. Reservoir samples were taken during aerosolization for particle sizing.

Figure 1:
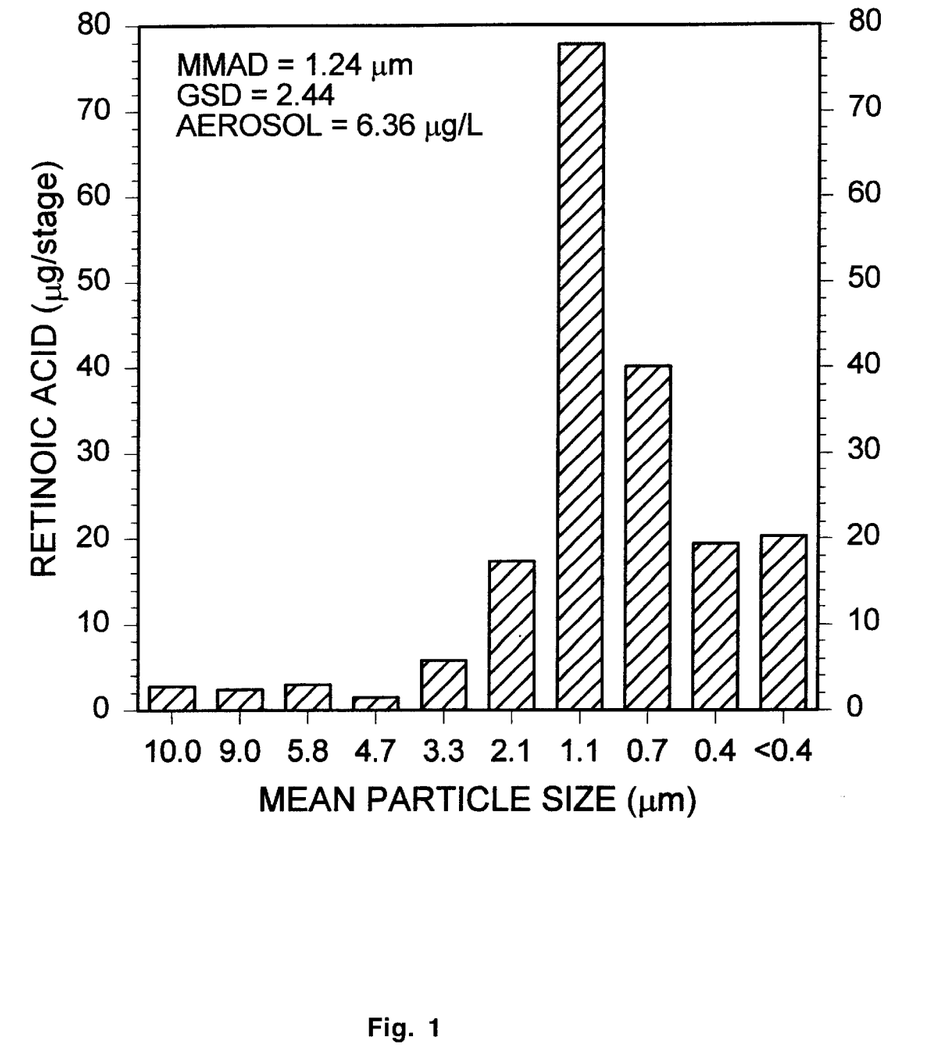
FIG. 1 shows the aerosol characteristics of L-ATRA. The particle size distribution of the L-ATRA aerosols was measured using an Anderson cascade impinger. ATRA concentrations were measured by HPLC. The characteristics of the L-ATRA presented here are from one representative experiment.

The characteristics of the aerosol particle (such as their size and the amount of drug associated with them) generated by the nebulizer were also studied. The mass median aerodynamic diameter of the aerosol particles was 1.44 µm, with a geometric standard deviation of 2.6. The aerosol so generated contained on average 6.5 µg of ATRA/liter of aerosol (FIG. 1). On the basis of this value, the estimated retained amount of ATRA for a single 30-min treatment per day was calculated as follows (24, 26): estimated aerosol dosage retained=aerosol concentration (µg/liter)×minute volume (liter/min)×duration of treatment (min)×retention factor=6.5 µg/liter×0.025 liter/min×30 min×0.3=1.5 µg/ treatment.

Analysis of the collected aerosols by HPLC, showed that the ratio between retinoic acid and the lipids was at the initial value of 1:10 (data not shown), suggesting that L-ATRA retained its integrity throughout the process of aerosolization.

EXAMPLE 10
Levels of ATRA in the Lungs of Mice Exposed to L-ATRA Aerosol

Mice were exposed to L-ATRA-containing aerosol (0.5 mg of ATRA/ml) for thirty minutes. Mice were sacrificed at 15 minutes or halfway through exposure, at the end of exposure (30 min), and at different times ranging from 1 hour to 96 hour after exposure. For each time point, 3–4 mice were sacrificed, and the lungs were used individually for drug analysis. The extraction efficiency of ATRA from lung using buffer and methanol was determined to be 80%.

Figure 2A:
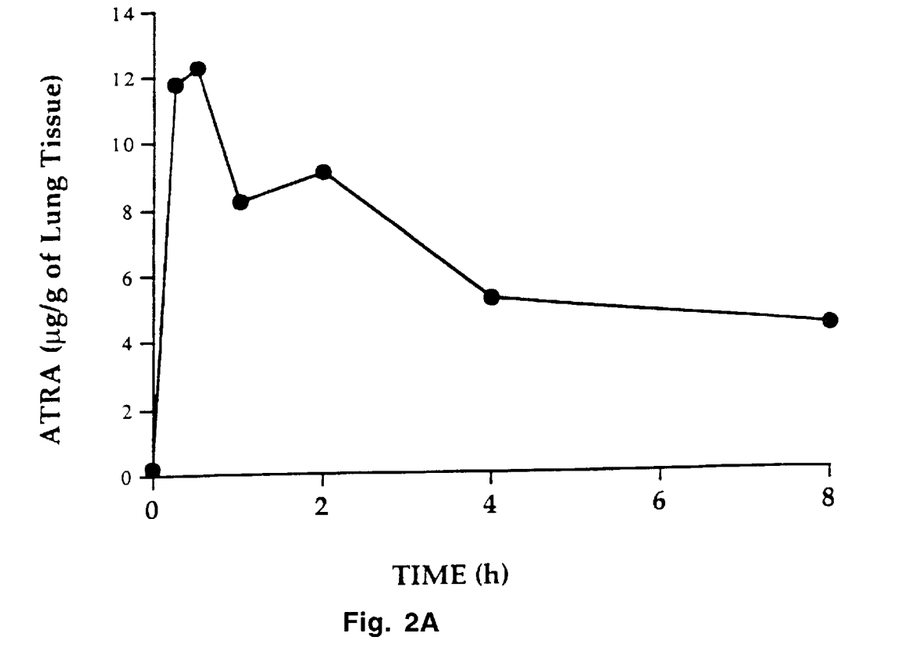
Figure 2B:
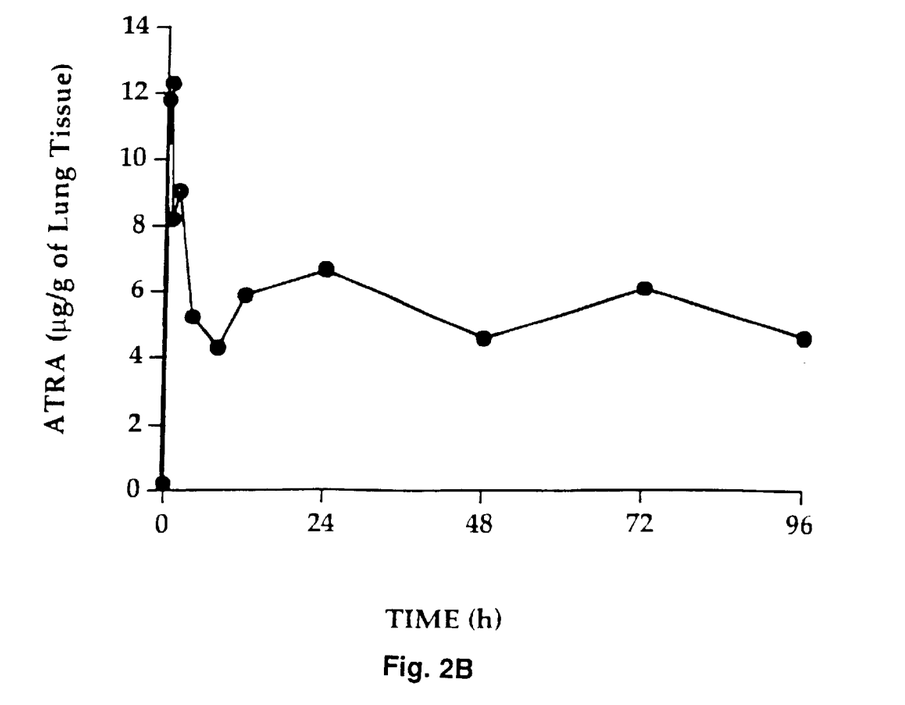

Analysis of the lung samples by HPLC indicated that the highest levels of ATRA (10±2 µg/g) were observed at the end of treatment, i.e., 30 min (FIG. 2A). Two hours after treatment, drug levels dropped to about 5–6 µg/g, after which, the levels were maintained until 96 hours (FIG. 2B). The first half life of ATRA in the lungs ($T_{1/2}\alpha$) was 1.25 hours; and the second half life from 1–96 hours ($T_{1/2}\beta$) was 6.1 hours. Lungs from untreated control mice showed a moderate level of ATRA (0.2±0.002 µg/g).

These results suggest that ATRA, when incorporated in liposomes, can be delivered by aerosolization, and the retinoic acid thus delivered is retained at levels of 5±0.2 µg of ATRA/g of lung tissue at least until 96 hours after treatment. Blood and liver samples showed no detectable levels of ATRA after aerosol L-ATRA treatment, suggesting that the drug is retained predominantly in the lung tissue.

EXAMPLE 11
Mice Exposed to Multiple Doses of L-ATRA Aerosol

Figure 3:
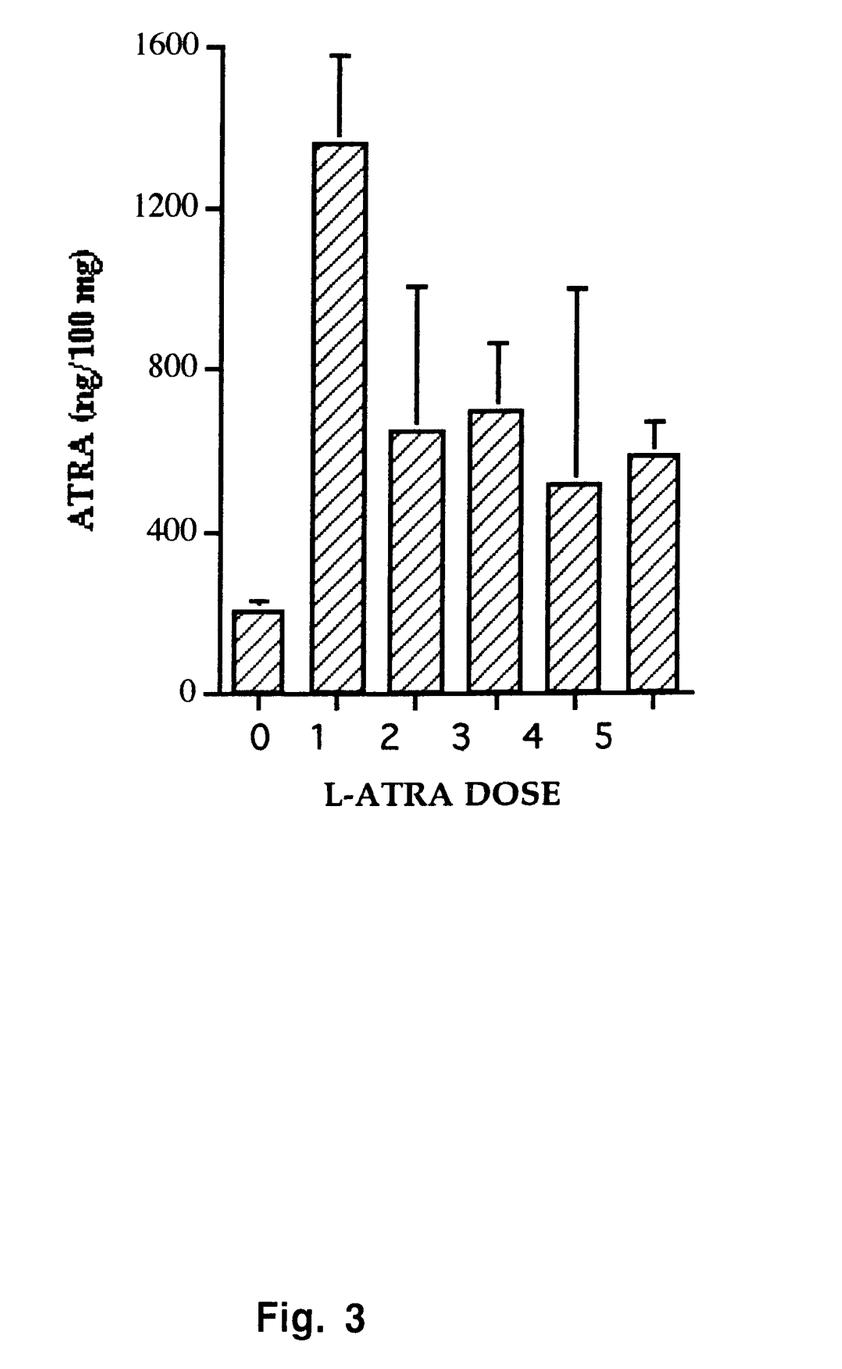
FIG. 3 shows ATRA in the lungs of mice exposed to multiple doses of aerosolized L-ATRA. Mice were exposed to aerosolized L-ATRA for 30 minutes daily for 5 consecutive days. After each dose, four mice were sacrificed and the lungs were analyzed for ATRA. Mean ATRA levels are presented (µg/g tissue).

A group of mice was administered aerosolized L-ATRA for 30 min everyday for 5 consecutive days. At the end of each treatment, the animals were sacrificed, and the lungs were extracted for ATRA determination. The results obtained showed that after the first treatment, the mean level of ATRA in the lungs was 13.2 µg/g of tissue. After administration of the second dose, the levels of ATRA were about 6.8 µg/g tissue and remained at 6±2 µg/g level even after five treatments (FIG. 3). Thus, multiple treatments for 5 consecutive days did not cause any greater accumulation of ATRA compared to the single treatment.

EXAMPLE 12
Uptake of L-ATRA

Figure 4A:
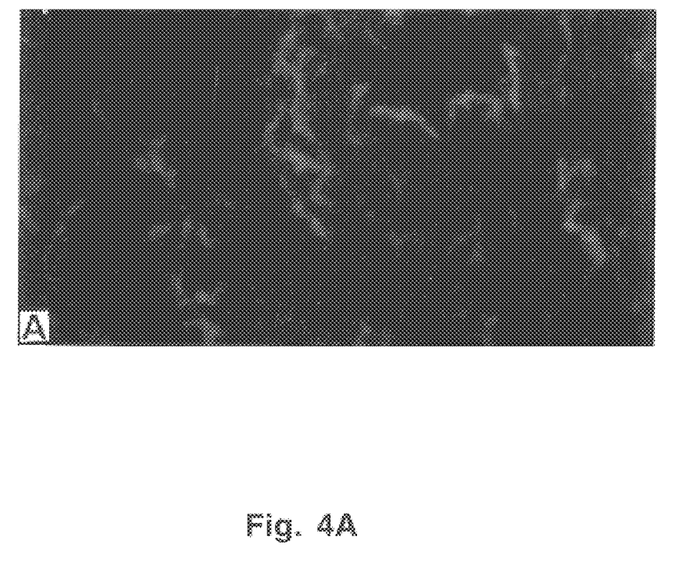
FIG. 4A shows a section of lung from an untreated mouse.
Figure 4B:
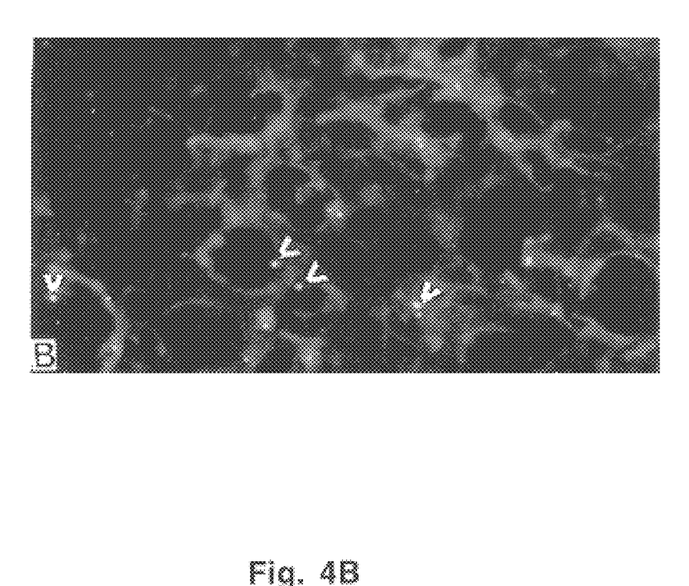
In FIG. 4B, aerosolized liposomes are observed in a section of lung from mice exposed to a single dose of aerosolized L-ATRA containing a fluorescent tagged lipid.
Figure 5A:
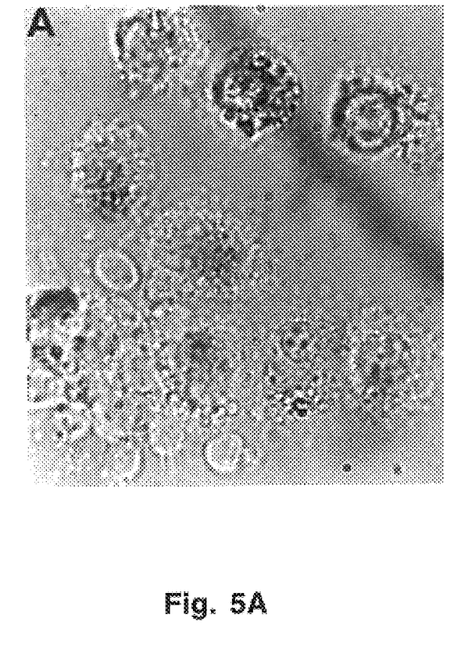
Figure 5B:
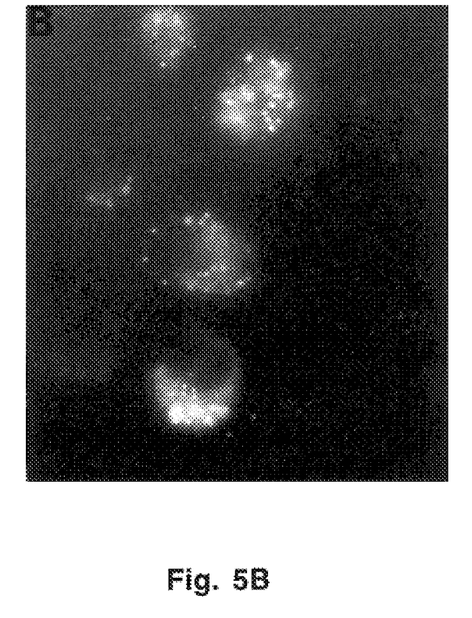

On observing a section of lung from mice exposed to aerosolized L-ATRA for 30 min, fluorescent liposomes can be found adhered to the pulmonary epithelial cells (FIG. 4). Also, lungs were removed from animals 1 hour after treatment and lavaged with cold medium. Cells were allowed to adhere to coverslips, and fluorescent liposomes could be observed within the cells (FIG. 5). Thus, in mice that inhaled aerosolized L-ATRA, deposits of liposomes in the lungs and alveolar macrophages were observed.

EXAMPLE 13
Biological Activity of Aerosolized L-ATRA

Alveolar macrophages express the enzyme tissue-type transglutaminase ($TGase_c$) (27). This enzyme is induced in response to retinoic acid treatment (28). Cell lysates of alveolar macrophages lavaged from treated and untreated mice were subjected to the TGase enzyme assay.

Figure 6:
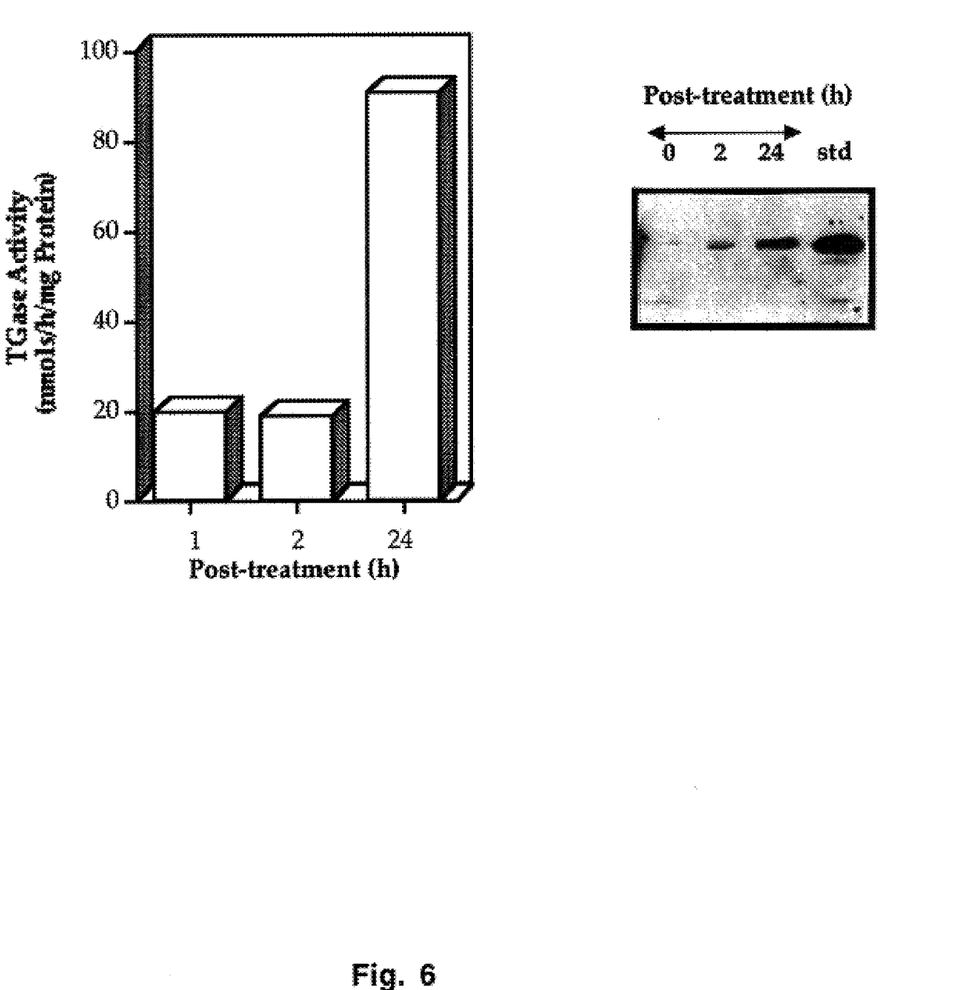
FIG. 6 shows $TGase_c$ activity and levels in alveolar macrophages of mice exposed to aerosolized L-ATRA. Mice were exposed to single doses of aerosol containing L-ATRA. After 2 hours or 24 hours, the mice were sacrificed and the macrophages lavaged. Macrophages were lysed, and the lysates were analyzed for enzyme activity (A) and for $TGase_c$ protein levels by western blotting. STD represents purified $TGase_c$ from guinea-pig liver.

The results shown in FIG. 6A demonstrate that alveolar macrophages from untreated animals have a low basal TGase activity (20 nmol/h/mg of protein). However, though cells from L-ATRA aerosolized mice sacrificed after 2 hours showed no appreciable increase in the levels of Tgase. However, 24 hours after treatment, the enzyme activity levels increased by 4.5 times (90 nmol/h/mg protein) (FIG. 6A). The increase in enzyme activity was due to ATRA alone, as 'empty liposomes' do not induce any TGase even at high concentrations (data not shown).

Moreover, immunoblot analysis of alveolar macrophage lysates, using anti-TGase antibody, revealed no detectable TGase protein from untreated mice or 2 hours post-treatment mice. However, 24 hours post-treatment the alveolar macrophages showed significant accumulation in TGase protein levels. L-ATRA-induced TGase was identical to the purified TGase from guinea pig liver TGase, as suggested by the identical size of the immunoreactive band. Thus, the ATRA reaching the lungs was biologically active and could induce both the protein and activity levels of TGase.

EXAMPLE 14
Direct Delivery of L-ATRA to the Aerodigestive Tract

Free ATRA due to its lipophilic properties cannot be aerosolized, therefore, its incorporation in liposomes provides an efficient way for the drug to be delivered by aerosols to the lung and upper aerodigestive tract. Administration of L-ATRA by aerosols results in direct delivery of ATRA to the tumor-bearing areas of the aerodigestive tract and lungs.

The L-ATRA was homogenous in size after aerosolization and maintained its integrity during the aerosolization process. After a single dose of aerosolized L-ATRA, mice were able to retain about 5 µg of ATRA/g of lung tissue, for up to 96 hours. Liposomes incorporating the drug as well as a fluorescent lipid marker could be located in lung sections (FIG. 4), as well as within alveolar macrophages lavaged from treated mice (FIG. 5). It has already been shown that liposomes bearing a positive or negative charge accumulated in the lungs to a greater extent than neutral vesicles (29).

EXAMPLE 15
L-ATRA Accumulation in the Aerodigestive Tract is Efficient and Nontoxic Gilbert et al., (24) have demonstrated that antiviral drugs like enviroxime when incorporated in liposomes and delivered by aerosols can accumulate to significant levels in the lungs. The drug accumulation was preferentially seen in the epithelial cells lining the bronchi and the bronchioles.

The present study demonstrates that L-ATRA delivered by aerosolization accumulates in lungs to a great extent and, more importantly, retains its biological activity as revealed by increased expression and activity of $TGase_c$ in alveolar macrophages of treated mice. It has been demonstrated that aerosol administration of amphotericin B-liposomes significantly increases both the mean time of survival and percent survival in mice with systemic infections of Candida (30).

Multiple treatments were undertaken to study the possibility of increasing the levels of ATRA delivered to the lungs. In these studies, multiple treatments (single dose every day for 5 days) did not show greater accumulation of ATRA in the lungs when compared with single treatment (FIGS. 3, 4). Daily treatment for 5 days may induce enhanced clearance of L-ATRA from the lungs probably due to the induction of RA-metabolizing enzymes such as hp450RA1. hp450RA1 was recently cloned and has been shown to be acutely induced in response to ATRA treatment in non-small cell lung carcinoma (31).

Based on these observations, weekly treatment over an extended period of time may be able to achieve higher levels of ATRA in the target tissues. No gross or microscopic pathologic changes were observed in the lungs of mice treated with single or multiple doses of aerosolized L-ATRA. Liver function tests were normal, demonstrating that L-ATRA was nontoxic. Gilbert (30), Wyde (32), and Waldrep (33) have also shown that exposure to liposome aerosols caused no adverse effects in mice and humans. Our results suggest that aerosol delivery of L-ATRA could be an efficient and non-toxic way of delivering higher levels of drug to treat cancers of the upper aerodigestive tract and lungs. Further evaluation in animal models should provide support for using this mode of delivery in clinical settings.

The following references were cited herein:
1. Lotan R (1980) Effects of vitamin A and its analogs (retinoids) on normal and neoplastic cells. Biochim Biophys Acta 605:33
2. Meyskens et al., (1987) 13-cis retinoic acid: Pharmacology, toxicology and clinical applications for the prevention of human cancer. Crit Rev Oncol Hematol 3:75
3. Mori S (1922) The changes in the para-ocular glands which follow the administration of diets low in fat-soluble A: with notes on the effect of the same diet on the salivary glands and the mucosa of the larynx and trachea. Bull Johns Hopkins Hosp 33:357
4. Wolbach S B, Howe P R (1925) Tissue changes following deprivation of fat-soluble-A-vitamin. J Exp Med 42:753
5. Meng-er et al., (1988) Use of all-trans-retinoic acid in the treatment of acute promyelocytic leukemia. Blood 72:567
6. Lippman et al., (1992) 13-cis-retinoic acid plus interferon α2a: highly active systemic therapy for squamous cell carcinomas of the cervix. J Natl Cancer Inst 24:241
7. Lippman S M, Parkinson D R, Itri L M, Weber P S, Schantz S A, Ota D M, Schusterman M A, Krakoff I H, Gutterman J U, Hong W K (1992) 13-cis-retinoic acid plus interferon α2a: effective combination therapy for advanced squamous cell carcinoma of the skin. J Natl Cancer Ins 84:235
8. Boring et al., (1993) Cancer Statistics. CA Cancer J. Clin. 43:7
9. Lippman et al., (1987) Retinoids as preventive and therapeutic anticancer agents. Cancer Treat Rep 71:391, 493
10. Lippman et al., (1992) Retinoid chemoprevention of upper aerodigestive tract carcinogenesis. In: DeVita et al., (eds). Important Advances in Oncology. Lippincott Co., Pa., p 93
11. Hong et al., (1986) 13-cis retinoic acid in the treatment of oral leukoplakia. N Engl J Med 315:1501
12. Silverman A K, Ellis C N, Voorhees J J (1987) Hypervitaminosis A syndrome: a paradigm of retinoid side effects. J Am Acad Dermatol 16:1027
13. Parthasarathy et al., (1994) Interaction of liposome-associated all-trans-retinoic acid with squamous carcinoma cells. Cancer Chemo Pharmacol 34:527
14. Rahman A, More N, Schein P S (1982) Doxorubicin-induced chronic cardiotoxicity and its protection by liposomal administration. Cancer Res 42:1817
15. Kanta et al., (1994) Liposome encapsulated vincristine: preclinical, toxicological and pharmacologic comparison with free vincristine and empty liposomes in mice, rats and dogs. Anti-cancer Drugs 5(5):579
16. Mehta K(1989) Interaction of liposome-encapsulated retinoids with normal and leukemic cells. In: Reichert U and Shroot B (eds). Pharmacology of the skin. Karger, Basel, p 74
17. Mehta et al., (1989) Effect of liposome encapsulation in toxicity and antifungal activity of polyene antibiotics. In: Berestein et al., (eds). Liposomes in the therapy of infectious diseases and cancer. New York, N.Y. p 263
18. Mehta et al., (1994) Liposome encapsulation circumvents the hepatic clearance mechanisms of all-trans-retinoic acid. Leuk Res 18:587
19. Estey et al., (1996) Alterations in tretinoin pharmacokinetics following administration of liposomal all-trans-retinoic acid. Blood 87(9):3650
20. Parthasarathy et al., (1998) Altered metabolism of all-trans-retinoic acid in liposome-encapsulated form. Cancer Letters, in press
21. Weinstein J N, Leserman L D (1984) Liposomes as drug carriers in cancer chemotherapy. Pharmacol Ther 24:207
22. Gilbert B E, Wyde P R, Wilson S Z, Robins R K (1991) Aerosol and intraperitoneal administration of ribavarin and ribavarin triacetate: pharmacokinetics and protection of mice against intracerebral infection with influenza A/WSN virus. Antimicrob Agents Chemother 35(7):1448
23. Vidgren et al., (1995) A study of $^{99m}$technetium-labelled beclamethasone dipropionate dilauroylphosphatidylcholine liposome aerosol in normal volunteers. Int J Pharmaceut 115:209
24. Gilbert B E, Six H R, Wilson S Z, Wyde P R, Knight V (1988) Small particle aerosols of enviroxime-containing liposomes. Antiviral Res 9:355
25. Poddar et al., (1991) Retinoic acid suppression of squamous differentiation in human head-and-neck squamous carcinoma cells. Int J Cancer 42:1817
26. Phalen R F (1984) Inhalation studies: foundation and techniques, CRC Press Inc., Boca Raton, Fla., p 222
27. Roth W J, Chung S I, Janoff A (1986) Inactivation of alveolar macrophage transglutaminase by oxidants in cigarette smoke. J Leuk Biol 39(6):629
28. Murtaugh M P, Mehta K, Johnson J, Myers M, Juliano R L, Davies P J (1983) Induction of tissue transglutaminase in mouse peritoneal macrophages. J Biol Chem 258:11074
29. Fidler et al., (1980) Design of liposomes to improve delivery of macrophage augmenting agents to alveolar macrophages. Cancer Res 40:4460
30. Gilbert et al., (1994) Aerosolized amphotericin B-liposomes for treatment of systemic candida infection in mice. Antimicrob Agents Chemo 38(2):356
31. White et al., (1997) cDNA cloning of human retinoic acidmetabolizing enzyme (hP450RAI) identifies a novel family of cytochromes P450 (CYP26). J Biol Chem 272(30):18538
32. Wyde et al., (1988) Activity against rhinoviruses, toxicity and delivery in aerosol of enviroxime in liposomes. Antimicrob Agents Chemo 32(6):890
33. Waldrep et al., (1997) Pulmonary delivery of beclamethasone liposome aerosol in volunteers: tolerance and safety. Chest 111:1

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of delivering a chemotherapeutic retinoid to the upper aerodigestive tract of an individual in need of such treatment, comprising the steps of:
   a) forming liposomes containing 0.1 to 10 mg/ml of a retinoid;
   b) resuspending said liposomes as an aqueous suspension;
   c) forming an aerosol of said suspension comprising 1.0 to 100 µg retinoid per liter of aerosol; and
   d) administering said aerosol to said individual by inhalation.

2. The method of claim 1, wherein said retinoid is selected from the group consisting of all-trans-retinoic acid (ATRA), 13-cis retinoic acid, 9-cis retinoic acid and 4-HPR.

3. The method of claim 1, wherein said liposomes are comprised of dipalmitoylphosphatidylcholine and stearylamine.

4. The method of claim 3, wherein dipalmitoylphosphatidylcholine and stearylamine are present in said liposomes at a ratio of 9:1 w/w.

5. The method of claim 3, wherein all-trans-retinoic acid is incorporated into said liposomes at a drug:lipid ratio of 1:10 (w/w).

6. The method of claim 1, wherein said aerosol is formed with a jet nebulizer.

7. The method of claim 6, wherein said aerosol consists of particles having an aerodynamic diameter of 1 to 3 microns.

8. The method of claim 7, wherein said aerosol particles contain liposomes having an average diameter ranging from 100 to 1000 nm.

9. The method of claim 1 wherein said method is used for the treatment of tumors of the upper aerodigestive tract.

10. The method of claim 1 wherein said method is used for the treatment of tumors of the lungs.

11. The method of claim 1 used to administer a systemic dose of retinoid by absorption of said retinoids through the lungs.

12. The method of claim 1, wherein said aerosol is inhaled for a period of time ranging from 5 minutes to 2 hours.

13. The method of claim 1, wherein said retinoid is administered in a series of treatments.

14. The method of claim 13, wherein said retinoid is administered at a frequency of two to three times per week.

15. The method of claim 13, wherein said series of weekly treatments results in the maintenance of a level of ATRA in the lungs of 0.05 to 20 µg ATRA/gram of lung tissue.

* * * * *

UNITED STATES PATENT AND TRADEMARK OFFICE
CERTIFICATE OF CORRECTION

PATENT NO. : 6,334,999 B1 Page 1 of 1
DATED : January 1, 2002
INVENTOR(S) : Brian E. Gilbert, Ranjani Parthasarathy and Kapil Mehta It is certified that error appears in the above-identified patent and that said Letters Patent is hereby corrected as shown below:

Column 4,
Line 45, "an" should read -- a --.
Line 64, "tearylamine" should read -- stearylamine --.

Column 5,
Line 48, "cmx4.66" should read -- cm x 4.66 --.

Column 7,
Line 25, "hour" should read -- hours --.

Column 8,
Line 14, please insert a comma after "though".

Column 12,
Line 10, please insert the word -- type -- between the words "jets" and "nebulizer"

Signed and Sealed this

Seventh Day of January, 2003

JAMES E. ROGAN
*Director of the United States Patent and Trademark Office*